US008640703B2

(12) United States Patent
Broborg et al.

(10) Patent No.: US 8,640,703 B2
(45) Date of Patent: Feb. 4, 2014

(54) PATIENT CASSETTE WITH VARIABLE PATIENT CIRCUIT VOLUME

(75) Inventors: Stefan Broborg, Haninge (SE); Ulrika Bergqvist, Danderyd (SE)

(73) Assignee: Maquet Critical Care AB, Solna (SE)

( * ) Notice: Subject to any disclaimer, the term of this patent is extended or adjusted under 35 U.S.C. 154(b) by 538 days.

(21) Appl. No.: 12/743,048

(22) PCT Filed: Nov. 14, 2007

(86) PCT No.: PCT/EP2007/062313
§ 371 (c)(1),
(2), (4) Date: Aug. 23, 2010

(87) PCT Pub. No.: WO2009/062547
PCT Pub. Date: May 22, 2009

(65) Prior Publication Data
US 2010/0307490 A1    Dec. 9, 2010

(51) Int. Cl.
*A61M 15/00*    (2006.01)
*A61M 16/00*    (2006.01)
*A61M 16/10*    (2006.01)
*A62B 9/02*    (2006.01)

(52) U.S. Cl.
USPC ............. 128/205.14; 128/203.12; 128/205.24

(58) Field of Classification Search
USPC ............. 128/202.27, 203.12, 203.25, 203.28,
128/203.29, 204.18, 204.21, 204.26,
128/204.28, 205.13–205.17, 205.24,
128/205.27, 205.28; 137/908
See application file for complete search history.

(56) References Cited

U.S. PATENT DOCUMENTS

| 3,687,137 | A |   | 8/1972  | Johnson |
|-----------|---|---|---------|---------|
| 4,883,051 | A | * | 11/1989 | Westenskow et al. ... 128/204.21 |
| 4,905,685 | A |   | 3/1990  | Olsson et al. |
| 5,109,838 | A | * | 5/1992  | Elam ........................ 128/203.12 |
| 5,398,675 | A |   | 3/1995  | Henkin et al. |
| 5,471,979 | A |   | 12/1995 | Psaros et al. |
| 5,549,105 | A |   | 8/1996  | Bloch et al. |
| 6,152,133 | A |   | 11/2000 | Psaros et al. |
| 6,648,832 | B2 | * | 11/2003 | Orr et al. ........................ 600/532 |
| 7,621,272 | B2 | * | 11/2009 | Orr .......................... 128/205.12 |
| 8,267,081 | B2 | * | 9/2012  | Flanagan et al. .......... 128/203.16 |
| 2002/0104542 | A1 |   | 8/2002  | Castor et al. |
| 2004/0089297 | A1 |   | 5/2004  | Videbrink |
| 2005/0247316 | A1 | * | 11/2005 | Orr .......................... 128/205.12 |

OTHER PUBLICATIONS

"currently". Oxford English Dictionary. 2012. http://www.oed.com/view/Entry/46102?redirectedFrom=currently#eid (Oct. 14, 2012).*
"tidal volume". Stedman's Medical Dictionary. 28th ed. http://www.stedmansonline.com (Oct. 14, 2012).*

* cited by examiner

*Primary Examiner* — Jackie Ho
*Assistant Examiner* — Mark K Han
(74) *Attorney, Agent, or Firm* — Schiff Hardin LLP

(57) ABSTRACT

A flexible patient cassette that can be optimized for different types of breathing circuits, different drive circuits and different patient categories has a first inlet arranged to be connected to a drive circuit, and at least a second inlet arranged to be connected to a patient connector, the first and second inlets being pneumatically connected with each other through a gas conducting passage constituting a patient circuit having a certain volume. The patient cassette has a volume-varying arrangement for varying the patient circuit volume to allow that volume to be varied in dependence of at least one of the type of breathing circuit in which the patient cassette is used; the type of drive circuit to which the patient cassette is connected; the tidal volume of a patient connected to the patient connector.

12 Claims, 7 Drawing Sheets

PATIENT CASSETTE WITH VARIABLE PATIENT CIRCUIT VOLUME

BACKGROUND OF THE INVENTION

1. Field of the Invention

The present invention relates to a patient cassette for use in a modular rebreathing circuit, a modular rebreathing circuit system, and an anesthesia apparatus.

2. Description of the Prior Art

In the field of mechanical ventilation and breathing aid, there are different types of breathing circuits used to deliver a desired gas mixture to a patient. Some of these circuits are rebreathing circuits in which substantially all or a part of the gas exhaled by a patient during an exhalation is re-supplied to the patient during the following inhalation. Such rebreathing circuits are often used when expensive additive gases are administered to the patient besides the necessary life sustaining gas mixture. By re-supplying the exhaled gas to the patient, the additive gas not assimilated by the patient in previous inhalations may be absorbed during the following inhalation.

Situations in which rebreathing circuits are often used are, e.g., in treatment of severe cases of asthma wherein helium may be used as additive, in diagnostic computer tomography (CT) treatment wherein xenon may be used as contrast medium, and not least in inhalation anesthesia wherein different anesthesia gases may be used as additive to block the perception of pain and other sensations to, e.g., allow patients to undergo surgery.

There are rebreathing circuits adapted to isolate particular gas components in the exhalation gas and re-supply only the isolated components to the patient during the following inhalation. One such system is disclosed in U.S. Pat. No. 5,471,979 in which an anesthesia reflecting breathing circuit is described. During exhalation, the exhalation gas passes through an adsorption filter wherein the anesthetic that was not absorbed in the patient's lungs during the previous inhalation is adsorbed, while the majority portion of the exhalation gas passes through the filter and is evacuated from the breathing circuit. During the following inhalation, when a flow of breathing gas passes the adsorption filter from the opposite direction, the adsorbed anesthetic is desorbed from the adsorption material and re-supplied to the patient. That is, the adsorption filter operates as a reflector of anesthetics and is sometimes also referred to as an anaesthetic reflector.

One disadvantage with this type of rebreathing circuit is that the adsorption filter is unable to adsorb, and hence reuse, gases composed by small-sized molecules, such as oxygen ($O_2$), helium, and nitrous oxide/laughing gas ($N_2O$). Due to the inability to reuse these gases, a high flow of breathing gases is required. A high flow of breathing gases is undesirable not only because it implies high consumption of gases, it is also harmful to the environment since nitrous oxide is a greenhouse gas. Furthermore, a low breathing gas flow is desirable to better preserve tracheal heat and moisture, prevent soda lime granules in carbon dioxide absorbers from drying, and preserve patient body temperature.

Examples of prior-art breathing circuits arranged to reuse not only the anesthetic gases but the majority portion of all exhalation gases are shown in FIGS. 1A-1C. The breathing circuits 100A-C are breathing circuits of circle type, often simply referred to as circle systems, in which substantially all of the exhaled gas, after removal of carbon dioxide ($CO_2$), is re-supplied to the patient during inhalation.

The functionality of the prior-art circle systems 100A-C will now be described with the aid of reference numerals in the drawings, which reference numerals are the same in the different drawings when denoting circuit components having a similar functionality.

The circle systems 100A-C all have a drive circuit 101A-C arranged to assist or control the breathing of a patient 102 connected to the circle system, while at the same time provide for recirculation of the exhalation gases. FIG. 1A illustrates a circle system in which the drive circuit is a mechanical ventilator 106 which is arranged to deliver a controlled flow of drive gas which acts directly on the exhalation gases from the patient 102 via a volume reflector or an exchanger 108. During exhalation, the gases exhaled by the patient 102 pass through a patient connector 104 to which the patient 102 is connected, into an expiration leg 110, and further into the volume reflector 108. The ventilator 106 then initiates inhalation of the patient 102 by opening an inspiratory valve 111 through which a drive gas flow is delivered to the volume reflector 108 via an inspiratory portion 112. The drive gas, typically oxygen, "pushes" the exhalation gases back to the patient via an inhalation leg 113 and the patient connector 104. Before the exhalation gases are re-supplied to the patient, carbon dioxide is removed by a CO2 absorber 114 and additional fresh gas, typically comprising a mix of oxygen, nitrous oxide and anesthetic, are added from a fresh gas supply line 116. During the exhalation phase, the inspiratory valve 111 is closed and an expiratory valve 117 is opened to conduct the drive gas that is pushed out of the volume reflector 108 by the exhalation gases away from the circle system 100A through an expiratory portion 118 of the ventilator 106. The expiratory portion 118 of the ventilator is typically connected to a scavenging system for isolating the discharged gas, or to a recovery system for recovering at least some of the gas components in the discharged gas. The volume reflector 108 should preferably be designed so that a well-defined front is formed between the drive gas and the exhalation gases so that a minimum of mixing occurs between the gas volumes. During ventilation, this front between the drive gas and the exhalation gases is pushed back and forth in the volume reflector 108. This type of circle system comprising a volume reflector in which a drive gas acts directly on the gases exhaled from a patient is often referred to as a volume reflector system. It may also be called a Werner system after the inventor of U.S. Pat. No. 4,989,597, wherein such a system is described in more detail. The volume reflector or exchanger may also be called a Werner volume. Hereinafter, the terms volume reflector and volume reflector system will be used.

In FIG. 1B, the drive circuit 101B is a breathing bag 120 which is manually maneuvered by a medical professional. During exhalation, the exhalation gases flows through the patient connector 104, the expiration leg 110 and into the breathing bag 120. The medical professional then initiates inhalation by compressing the breathing bag 120, which compression re-supplies the exhalation gases to the patient via the inspiration leg 112, in which CO2 is removed and additional fresh gas added, and via the patient connector 104. The circle system 101B also comprises a pressure regulating valve 122 through which excess gases can leave the breathing circuit 100B. Typically, the excess valve 122 is an adjustable pressure limiting (APL) valve which serves to set a highest allowable pressure in the circle system 101A and hence limit the amount of pressure build-up that can occur during manual ventilation due to the compression of the breathing bag 120 and the supply of fresh gas via the fresh gas supply line 116. The APL valve 122 also serves to set a filling degree of the breathing bag 120. Just as the expiration valve 117 described above with reference made to FIG. 1A, the excess valve 122 is normally connected to a scavenging or recovery system to make sure that the excess gases leaving the circle system 101B do not harm attending medical personnel.

In FIG. 1C, the drive circuit 101C has a ventilator 106 and a resilient bellows 124 which is contained in a container 126. The ventilator 106, has an inspiratory portion 112 and an expiratory portion 118 arranged in fluid communication with the container 126 to pneumatically operate the resilient bellows 124 and thereby control the breathing of a patient 102 connected to the system 101C. The resilient bellows 124 in the container 124 is often referred to as a "bag-in-bottle". The functionality of the circle system 101C is very similar to the functionality of the circle system 101B described above with reference made to FIG. 1B. They differ mainly in that the compressible reservoir that collects and re-supplies the exhalation gases is manually operated in circle system 101B (breathing bag 120) while it is automatically operated in circle system 101C (resilient bellows 124) by means of an automatic ventilator. The circle system 101B also comprises an excess valve 128, typically a pop-off valve 128, which is arranged to open if the resilient bellows or bag-in-bottle 124 hits the roof of the container 126.

It should be noted that most breathing apparatuses of today offers both a manual and an automatic ventilation mode. That is, most breathing apparatuses comprise a manual bag and, e.g., a bag-in-bottle arrangement allowing the medical professional to choose between manual or automatic ventilation by turning a control knob or the like on the breathing apparatus. The drive circuits 101-C have herein been illustrated in different drawings only to facilitate understanding of the functionality of the different breathing circuits 100A-C. Those skilled in the art appreciate how to re-design any of the circle systems 100A and 100C to allow a manual bag 120 to be used as a complementary drive circuit to any of the drive circuits 101A or 101C.

Circle systems of the above mentioned types all suffer from drawbacks when it comes to ventilating different patients having different lung capacities. All the illustrated prior-art circle systems 101A-C have some kind of collector for exhalation gases. In system 101A the collector is an open-ended collector in form of the volume reflector 108, in system 101B the collector is a manual breathing bag 120, and in system 101C the collector is a resilient bellows 124. If the collectors 108, 120, 124 have too small a volume compared to the gas volume expired by the ventilated patient at each breath, i.e. the tidal volume of the patient, some of the exhalation gases will leave the circle systems through the valves 117, 122, 128 which causes an undesired loss of exhalation gases one would like to re-supply to the patient. Not only does the loss of exhalation gases increase the consumption of, e.g., anesthetic gases, the increased fresh gas flow (FGF) required for compensating the losses also undesirably cools and desiccates the pulmonary system of the patient. However, if the volume of the collector 108, 120, 124 is too big, the excess collector volume will add to the volume of the breathing circuit connecting the collector 108, 120, 124 and the patient 102, and if the breathing circuit volume is big compared to the tidal volume of the patient, the responsiveness of the circle system 101A-C is decreased due to the large compressible volume in the circle system. It is easily understood that if, e.g., an infant patient having a tidal volume of 0.2 liters is connected to a circle system 101A-C having a breathing circuit volume of 2 liters, the large compressible volume will introduce system delays severely decreasing the accuracy in the control of the circle system. The poor control of the gas flows within the circle system so arising makes it hard to deliver a well-defined gas volume to the patient, and/or to deliver the gas at a well-defined pressure. The problem of too big collector volume is not as critical in the cases in which the collector is a resilient reservoir, such as the manual bag 120 or the resilient bellows 124, since their volume is adapted to the amount of gas filling them. However, it is highly important that the rest of the breathing circuit volume is small also in these cases.

In order to avoid some of the above problems associated with circle systems, it is known in the art to during manual ventilation use differently sized breathing bags when ventilating patients having different tidal volumes to ensure that the breathing bag can hold all the gas volume exhaled by the patient. It is, however, important not to use too big a bag in order to maintain a good feeling and "connection with the patient's lungs" when squeezing it. It is also known to decrease the volume of the patient connector 104 in order to decrease the volume of the breathing circuit connecting the collector 108, 120, 126 and the patient when ventilating infant or pediatric patients having small tidal volumes. For example, U.S. Pat. No. 5,393,675 discloses an anesthesia gas delivery system wherein the patient connector comprises a variable volume patient reservoir to decrease the volume of the patient connector when ventilating pediatric patients.

Most breathing circuit systems of today are modular breathing systems meaning that they comprise a plurality of separate modules that can be interconnected to constitute different types of breathing circuits. Such modular breathing systems typically comprise a drive circuit module, a patient circuit module and patient connectors. The drive circuit may be a mechanical ventilator, a manual bag or a bag-in-bottle arrangement, as described above with reference made to FIGS. 1A-C. The patient circuit module typically comprises the majority portion of the breathing circuit, non-return valves, carbon dioxide absorbers, additional filters, flow and pressure sensors, etc., and is often molded in one piece to be easily connected to, e.g., an anesthesia machine. Such a patient circuit module intended for interconnection between a drive circuit module and a patient connector is sometimes referred to as a patient cassette. U.S. Pat. No. 5,549,105 and EP 0919253B1 disclose examples of such patient cassettes, referred to as "closed circuit patient system" and "patient breathing circuit", respectively.

The type and functionality of a modular breathing circuit is generally determined by the configuration of the patient circuit comprised in the patient cassette. By connecting different patient cassettes with different patient circuit configurations to a breathing apparatus, e.g. an anesthesia machine, breathing circuits optimized for different respiratory treatments, different drive circuits and/or different patient categories can be obtained.

This implies that if a care institution wants to be able to provide respiratory treatment to both children and adult patients and have the choice to choose what drive circuit to use and what breathing circuit type to use, the care institution must have a number of patient cassettes at hand. Typically, however, care institutions have a standard patient cassette adapted for an adult patient, a particular breathing circuit type and a particular drive circuit.

It is thus a need for a more flexible patient cassette that can be optimized to different types of drive circuits and different patients, and which can be optimized for use in different breathing circuit types.

SUMMARY OF THE INVENTION

It is an object of the present invention to provide a flexible patient cassette which can be optimized for different types of breathing circuits, different drive circuits and different patient categories.

It is a further object of the invention to provide a modular rebreathing circuit system of circle type maximizing the rebreathing of additive gases by a subject connected to the system, which additive gases were not absorbed by the subject in previous inhalation phases, while maintaining a good accuracy in control and regulation of the system.

This object is achieved by providing a patient cassette for use in a modular rebreathing circuit system, said patient cassette comprises a first inlet arranged to be connected to a drive circuit, and at least a second inlet arranged to be connected to a patient connector, said first and second inlet being pneumatically connected with each other through a gas conducting passage constituting a patient circuit having a certain volume. The patient cassette comprises means for varying the patient circuit volume in dependence of at least one of the type of breathing circuit in which the patient cassette is used, the type of drive circuit to which the patient cassette is connected, the tidal volume of a patient connected to said patient connector.

By providing a patient cassette having a variable patient circuit volume, the patient cassette according to the invention can be adapted so as to suit the particular drive circuit and the particular patient between which it is connected.

By minimizing the patient circuit volume, the patient cassette can be advantageously used in a circle system driven by a manual bag or a bag-in-bottle arrangement, in which case the small patient circuit volume ensures good accuracy in control and regulation of the circle system. It can also be advantageously used in an open breathing circuit.

By increasing the patient circuit volume, a volume reflector can be introduced, allowing the patient cassette according to the invention to be advantageously used in a circle system of volume reflector type driven by e.g. a ventilator providing a flow of drive gas which acts directly on the gases exhaled by a patient.

By providing a volume-variable volume reflector, the patient cassette according to the invention can minimize undesired evacuation of exhalation gases which otherwise may occur in case the volume reflector is too small compared to the tidal volume of the ventilated patient, while at the same time maximize the responsiveness of the circle system which otherwise may be poor in case the volume reflector is too big compared to said tidal volume.

Preferably, the patient cassette includes a volume-varying arrangement to vary the volume of the common line of the patient circuit. The common line is the part of the patient circuit conveying breathing gases both to and from the patient, which will be described in more detail in the detailed description.

According to a preferred embodiment of the invention, the patient cassette has a connection arrangement for detachably connecting different gas containers with different volumes in-line with the common line of the patient circuit so as form a volume-variable part thereof.

Preferably, the patient cassette is designed so as to allow the different gas containers to be connected external to the patient cassette to allow easy exchange of said containers.

One preferred way to accomplish this is to provide the patient cassette housing with a third and a fourth inlet of which the third inlet is pneumatically connected to the at least first inlet and the fourth inlet is pneumatically connected to the at least one second inlet. The third and the fourth inlets are provided with connection means for connecting a gas container, such as a traditional breathing tube, there between, external to the patient cassette housing. Thereby, a gas conduit mounted externally and detachably to the patient cassette housing closes the patient circuit and forms a volume-variable part thereof, of which volume can be altered simply by connecting tubes of different lengths between said third and fourth inlets.

Preferably, the patient cassette comprises a valve arrangement and a secondary gas flow path to allow the gas flow within the patient circuit to bypass the above described gas container between said third and fourth inlet when there is a desire to minimize the patient circuit volume. Thereby, the patient cassette can be optimized for use in a circle system driven by manual bag or a bag-in-bottle arrangement. By arranging an anesthetic adsorption filter, or anesthetic reflector, within said secondary gas flow path, the patient cassette according to the invention can also be adapted for use in an anesthetic reflector system. That is, a breathing circuit in which anesthetic in the exhalation gases can be reused while the majority portion of the exhalation gases are vented out of the breathing circuit.

The patient cassette housing may be arranged to enclose the entire patient circuit. According to one embodiment of the present invention, the entire patient circuit is arranged within the housing which comprises a lid or at least means enabling easy access to the interior of the patient cassette housing. The patient cassette has a connection arrangement for easily detaching a gas conduit portion forming a part of the patient circuit, and attaching another gas conduit portion with a different length or thickness inline with the patient circuit, so as to vary the patient circuit volume in the patient cassette. This gives the advantage of a patient cassette having no external gas containers or gas conduits.

According to another embodiment of the invention, the common line of the patient circuit has a number of parallel gas flow paths having different volumes. By directing the gas flow in the patient circuit through one or the other of said paths, the patient circuit volume can be varied. By directing it through a gas flow path having a large volume, the patient cassette is optimized for being used in a volume reflector system connected to a patient having a large tidal volume, and by directing it through a gas flow path having a slightly smaller volume, the patient cassette is optimized for being used in a volume reflector system connected to a patient having a smaller tidal volume. By directing the gas flow through a gas flow path having a very small volume, the volume of patient circuit is minimized and the patient cassette is thus optimized to be used in a circle system driven by a manual bag or a bag-in-bottle arrangement, or to be used in an anesthetic reflector system.

According to another embodiment of the invention, the patient circuit is made of "coaxial" gas tubes. Coaxial gas tubes should herein be interpreted as a tube arrangement wherein a thin inner gas tube is surrounded by at least one thicker outer gas tube. The patient cassette includes pathways for conducting the gas flow through the patient circuit through the inner, the outer, or both of said gas tubes. Thereby, the patient circuit volume can be made really small when ventilating infant patients, in which case the bigger flow resistance caused by thin gas tubes is not as crucial to the system performance as when ventilating patients with big tidal volumes.

The patient cassette can include a volume-varying arrangement for varying the patient circuit volume automatically. According to one embodiment of the invention, the patient cassette has a user interface for inputting the desired patient circuit volume, and control components for automatically altering the patient circuit volume based on the information input by the user.

The patient cassette may also include a volume-varying arrangement for allowing the patient circuit volume to be varied based on measurement values from sensors arranged within the breathing circuit. According to one embodiment of the invention, the patient cassette includes a component, such as a flow meter, for measuring the tidal volume of the patient connected to the patient cassette, and/or the gas volume leaving the breathing circuit via an expiratory portion of the breathing circuit. The patient cassette may include a display for displaying the measured value(s) to a system operator in order for the operator to manually vary the volume of the patient circuit based on the measured values, or, the patient cassette may comprise means for automatically adjust the volume of the patient circuit based on one or both of the measured volumes.

Preferably, the patient cassette includes a volume-varying arrangement for altering the volume of the patient circuit continuously so as to always be able to use the optimal patient circuit volume for each patient.

According to another embodiment of the present invention, in which the patient cassette has a connection arrangement for detachably connecting different gas containers with different volumes in-line with the common line of the patient circuit to form a volume-variable volume reflector, the detachable gas container also embodies a material that adsorbs anesthetic gases. When the exhalation gases passes through the volume reflector, the anesthetic agent is adsorbed by the adsorption material, and when the exhalation gas is pushed back to the patient by the drive gas during the following inhalation, the anesthetic gases are desorbed and re-supplied to the patient. The additional absorber ensures that even if a small amount of exhalation gas is evacuated from the circle system, nearly all anesthetic gas in the exhalation gas can still be re-supplied to the patient. This feature is particularly important if the volume reflector happens to be a little bit too small compared to the tidal volume of the currently ventilated patient. However, a small amount of exhalation gas typically leaves the breathing system even if the volume of the volume reflector is optimized for the currently ventilated patient and the combined volume and anesthetic reflector thus serves to always maximize rebreathing of anesthetic gases.

BRIEF DESCRIPTION OF THE DRAWINGS

The present invention will become more fully understood from the detailed description provided hereinafter and the accompanying drawings, which are not necessarily to scale, and are given by way of illustration only. In addition, the use of spatial terms such as top, bottom, above, below etc. is for ease of explanation and should not be construed as structural or orientation limitations.

DESCRIPTION OF THE PREFERRED EMBODIMENTS

In the following description, for purposes of explanation and not limitation, specific details are set forth, such as particular breathing circuit components, in order to provide a thorough understanding of the present invention. However, it will be apparent to one skilled in the art that the present invention may be practiced in other embodiments that depart from these specific details. In other instances, detailed descriptions of well-known breathing circuit configurations and breathing circuit components are omitted so as to not obscure the description of the present invention with unnecessary detail.

Figure 2:
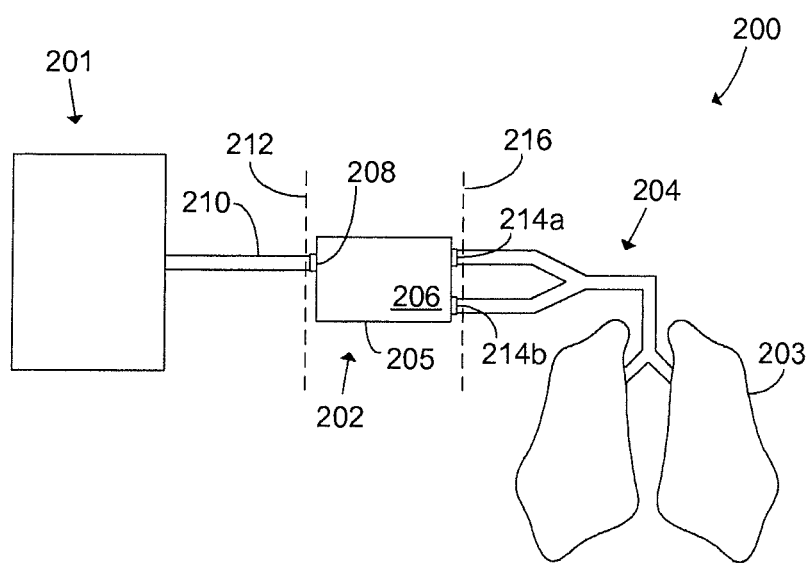
FIG. 2 schematically illustrates a modular breathing circuit system according to the invention.

FIG. 2 schematically illustrates a modular breathing circuit system 200 according to the invention. The breathing circuit can be seen as having three different parts or modules. The first module is a drive circuit module 201 which is responsible for controlling the ventilation of a patient 203 connected to the breathing circuit 200, and for re-supplying the exhalation gases to the patient during inhalations to come. The drive circuit 201 is connected to the second module which is a patient circuit module 202 typically comprising the majority portion of the breathing circuit, non-return valves, carbon dioxide absorbers, sensors, etc. The third module is a patient connector 204 which connects the patient 203 to the patient circuit module 202.

The drive circuit 201 may be a manual breathing bag, a ventilator, a so called bag-in-bottle arrangement which comprises a resilient bellows whose contractions are mechanically or pneumatically controlled by a ventilator, or any other circuit or device that is arranged to control the ventilation of a patient.

The patient circuit module 202 has a housing 205 to form a well-defined body, hereinafter referred to as patient cassette 206, which can be easily interconnected between different drive circuits 201 and patient connectors 204. The housing 205 of the patient cassette 206 is typically a plastic box molded in one piece to form a regular patient cassette 206, but may of course be shaped differently and be made out of other materials than plastic. The patient cassette 206 may also comprise a plurality of molded pieces assembled together. The patient cassette housing 205 has a first inlet 208 to which the drive circuit 201 is pneumatically connected, typically by means of a standard gas tube or conduit 210, or by any other connection interface. The inlet 208 of the patient cassette 206 hence form the interface between the drive circuit module 201 and the patient circuit module 202, which interface is illustrated with a dashed line denoted by reference numeral 212. The patient cassette 206 further has at least a second inlet 214a-b to which the patient connector 204 is connected. The patient cassette may have a single second inlet 214a to which a patient connector conveying a bidirectional flow to and from the patient is connected, but preferably the patient cassette 206 comprises two second inlets 214a and 214b to which an exhalation branch and an inhalation branch, respectively, of a Y-shaped patient connector is connected. Thereby, the volume of the breathing circuit in which a bidirectional flow must be conveyed is minimized, thus minimizing what is often referred to as dead space in the context of breathing circuits. The at least one second inlet 214a-b of the patient cassette 206 hence form the interface between the patient circuit module 202 and the patient connector 204, which interface is illustrated with a dashed line denoted by reference numeral 216.

The patient connector 204 typically has a patient tube or similar connected at one end to the inlet(s) 214a-b of the patient cassette 206 as described above, and a connector that connects the other end of the tube to the patient 203, such as a face mask or a tracheal tube. Typically, it also has ports for inserting one or several sensors so as to allow the gas inhaled and exhaled by the patient to be analyzed in various ways.

The patient cassette 206 has a gas conducting passage or gas channel (not shown) pneumatically connecting the first inlet 208 and the at least one second inlet 214a-b. This gas conducting passage will hereinafter be referred to as the patient circuit, and the patient cassette 206 according to the invention comprises means for varying the volume of said patient circuit. By varying the patient circuit volume, the patient cassette 206 can be optimized for use in different types of breathing circuits, optimized for different drive circuits, and optimized for different patients, as will be apparent from the description of preferred embodiments following below.

The modular breathing circuit system 200 is typically used in inhalation anesthesia treatment but is advantageously used whenever there is a desire to reuse gas that was not assimilated by the patient in previous inhalations. For example, the system 200 may be used in treatment of asthma wherein helium may be used as additive, in diagnostic computer tomography treatment wherein xenon may be used as contrast medium, or in any treatment in which nitrous oxide is supplied to the patient. However, for simplicity and not limitation, the breathing circuit 200 will now be described when functioning as a modular anesthesia machine.

During the following description of preferred embodiments of the invention, reference will be made to FIGS. 3-7 in which similar circuit components have been denoted by like reference numbers, differing only in the hundreds digits which has been set equal to the number of the drawings in which they are found. These reference numbers have also, as far as possible, been chosen to correspond to the reference numbers used in FIG. 2. The function of the different circuit components differing only in the hundreds digit is the same unless explicitly stated otherwise. It should be appreciated that a feature described with reference to a particular drawing typically is applicable also to other embodiments of the invention disclosed herein.

Figure 3:
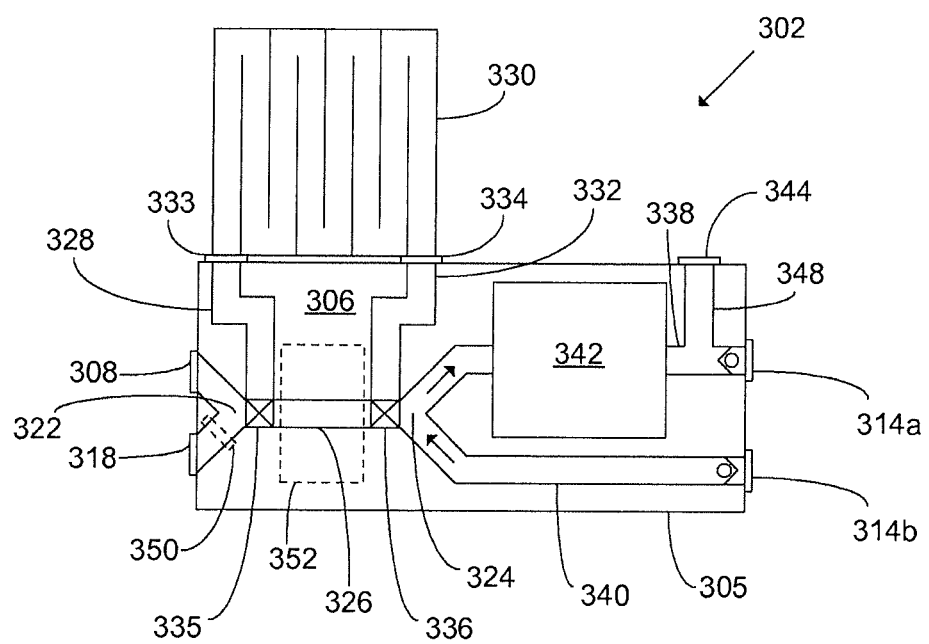
FIGS. 3 to 7 illustrate different embodiments of a patient cassette according to the invention.

With reference now made to FIG. 3, a patient circuit module 302 having a housing 305 to form a patient cassette 306 is shown. The patient cassette 306 has a first inlet 308 arranged to be connected to a drive circuit (not shown), such as a manual bag, a ventilator operated bag-in-bottle, or a direct-acting ventilator, and two second inlets 314a-b arranged to be connected to a an inhalation and exhalation branch, respectively, of a Y-shaped patient connector (not shown). The patient circuit of the patient cassette 306 will now be described.

In this embodiment, the patient cassette 306 has an outlet 318 that is pneumatically connected to the inlet 308 at a first branch point 322. The first branch point 322 is connected to a second branch point 324 via a common line that has a first 326 and a second 328, 330, 332 common-line portion. A common line should herein be construed as a gas conducting passage intended to convey gas in both directions, i.e. a gas line conducting a bidirectional gas flow. The second common-line portion 328, 330, 332 comprises a gas container 330 which is detachably connected external to the patient cassette housing 305 between a third 333 and a fourth 334 inlet of the patient cassette 306. Two two-way valves 335, 336 are arranged in the common line, close to the first 322 and the second 324 branch points, for directing the gas flow within the common line through either the first 326 or the second 328, 330, 332 common-line portion. At the second branch point 324, the common line is branched into an inspiratory leg 338 and an expiratory leg 340. The inspiratory leg 338 is connected to the outlet 314a which is arranged to be connected to the inspiratory branch of a Y-shaped patient connector, and the expiratory leg 340 is connected to the inlet 314b which is arranged to be connected to the expiratory branch of the same Y-shaped patient connector. The patient cassette 306 further comprises a carbon dioxide ($CO_2$) absorber 342, such as a soda lime canister, arranged to remove $CO_2$ from the gas passing through the inspiratory leg 338, and a fresh gas inlet 344 which is pneumatically connected to the inspiratory leg 338 via a fresh gas supply line 348 for delivering additional fresh gas, typically oxygen, nitrous oxide and anesthetic, to the gas flow passing there through.

Figure 1A:
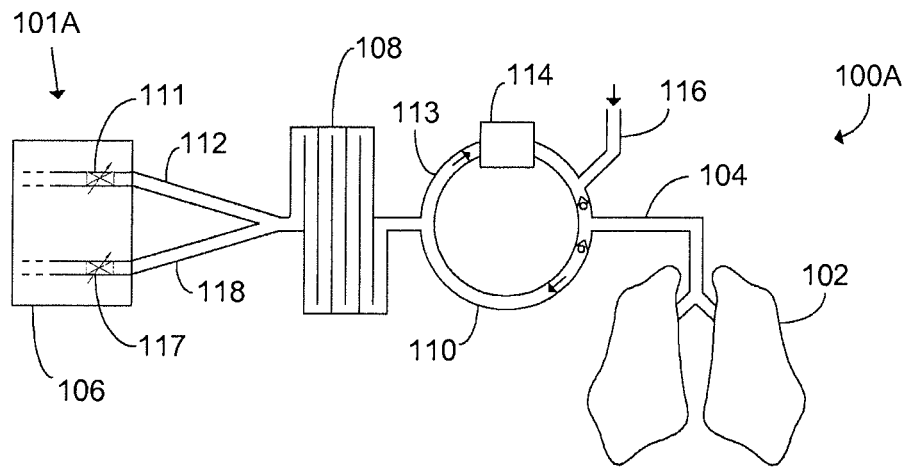
FIGS. 1A-C schematically illustrate different types of circle systems according to prior-art.

First, the function of the patient cassette 306 will be described when used in a circle system driven by a ventilator providing a controlled flow of drive gas which acts directly on the exhalation gases from the patient, i.e. a volume reflector system similar to the circle system 100A described in the background portion with reference made to FIG. 1A. Although not shown, the inlet 308 should hence be regarded as connected to an inspiratory portion of a ventilator, and the outlets 314a and 314b should be regarded as connected to an inhalation branch and an exhalation branch, respectively, of a Y-shaped patient connector which at the other end is connected to a patient via a face mask, a tracheal tube, or the like.

When the patient exhales, exhalation gases will enter the patient cassette 306 via the inlet 314b to which they are conveyed via the exhalation branch of the patient connector. The exhalation gases are conveyed through the expiratory leg 340 and into the second common line portion 332, 330, 328 to which they are directed by the two-way valve 336. To initiate inhalation, the ventilator delivers a flow of drive gas which enters the patient cassette via the inlet 308. The two-way valve 335 directs the drive gas flow into the second common line portion 328, 330, 332 in which a well-defined front between the drive gas and the exhalation gases is formed. The drive gas "pushes" the exhalation gases back through the second common line portion 328, 330, 332, into the inspiratory leg 338 and out through the inlet 314a from which it is conveyed to the patient via the inhalation leg of the patient connector. Before the exhalation gases are re-supplied to the patient, $CO_2$ is removed by means of the $CO_2$ absorber 342 and additional fresh gas is added to the gas flow via the fresh gas supply line 348 in the inspiratory leg 338.

The outlet 318 is typically connected to the expiratory portion of the ventilator and during the exhalation phase, the drive gas that is pushed out of the second common-line portion 328, 330, 332 by the exhalation gases is directed into said expiratory portion of the ventilator through the outlet 318. Often, an expiratory valve in the expiratory portion of the ventilator (comparable with the expiratory valve 117 in FIG. 1A) is configured to open at a predetermined pressure against which the patient exhales, thus constituting what is known in the art as a positive end expiratory pressure (PEEP) valve. The patient cassette 306 may comprise a valve arrangement 350 arranged between the first branch point 322 and the outlet 318, which valve arrangement 350 can comprise such a controllable PEEP valve. This is advantageous in case the outlet 318 is not connected to an expiratory portion of a ventilator but directly connected to atmosphere, a scavenging system for isolating the discharged gas, or to a recovery system for recovering at least some of the gas components in the discharged gas. In that way, a PEEP can always be applied to the patient connected to the circle system.

The second common-line portion 328, 330, 332 thus serves as a volume reflector in which a well-defined front between the drive gas and the exhalation gases is pushed back and forth. If the volume of the volume reflector formed by the common-line portion 328, 330, 332 is smaller than the tidal volume of the ventilated patient, not only the drive gas but also some of the exhalation gases following the drive gas will leave the circle system through outlet 318 during exhalation, causing an undesired loss of, e.g., expensive anesthetic gases that one would like to re-supply to the patient during the following inhalation and a demand for higher fresh gas flow through the fresh gas supply line 348 to compensate for the evacuated exhalation gases. If, on the other hand, the volume of the volume reflector formed by the common-line portion 328, 330, 332 is much bigger than the tidal volume of the ventilated patient, the compressible volume in the patient circuit is increased, causing decreased responsiveness of the circle system and decreased accuracy in the control thereof. Since the patient cassette 306 has a third and a fourth inlet 333 and 334 between which different gas containers having different volumes can be detachably connected to form a volume-variable portion 330 of the volume reflector 328, 330, 332, the volume reflector can be tailored so as to always suit the tidal volume of the currently ventilated patient. Preferably, the volume-variable portion 330 is chosen so that the total volume of the volume reflector 328, 330, 332 is equal to, or slightly bigger, than the tidal volume of the patient. The tidal volume of a patient can be roughly calculated as 6-7 ml per kilogram bodyweight. That is, the tidal volume and hence the recommended minimum volume of the volume reflector 328, 330, 332 may be approximately 0.1 liter for a pediatric patient weighing 15 kilos and 0.7 liter for a fully grown man weighing 100 kilos. It should be pointed out that the volume of a typical patient circuit (any volume reflector excluded) may be approximately 0.2 liters. It should also be noted that the CO2 absorber and any other additional circuit component of which main purpose is something else than just conducting gas are not a part of what is herein referred to as the patient circuit.

It should be noted that the inlet 308 also may be connected to a common line of the ventilator, which common line is branched into an inspiratory portion and an expiratory portion of the ventilator, respectively, outside the patient cassette 306. In such a case, the point of the breathing circuit corresponding to the first branch point 322 in FIG. 3 is situated external to the patient cassette 306. Since the volume reflector is the volume of the common line between said first branch point and the second branch point 324, this implies that some of the volume reflector is located outside of the patient cassette 306 and rather is to be regarded as a part of the drive circuit. Nevertheless, there is still a need to vary the volume of the volume-reflector portion comprised in the patient cassette 306 so as to adapt the total volume of the volume reflector to the tidal volume of the patient. In this case, the outlet 318 of the patient cassette 306 is redundant and can be held closed.

The gas container 330 in the illustrated embodiment depicts a plastic box comprising a folded gas conducting passage. However, in its simplest form, the gas container 330 could be a traditional breathing tube and the volume of the common-line portion 328, 330, 332 can be varied simply by attaching breathing tubes of different lengths between the third 333 and the fourth 334 inlet of the patient cassette 306. It should be noted that the cross section area of the gas conducting passage in the gas container 330 should not be too big in order for the front between the drive gas and the exhalation gas to be well-defined.

Figure 1B:
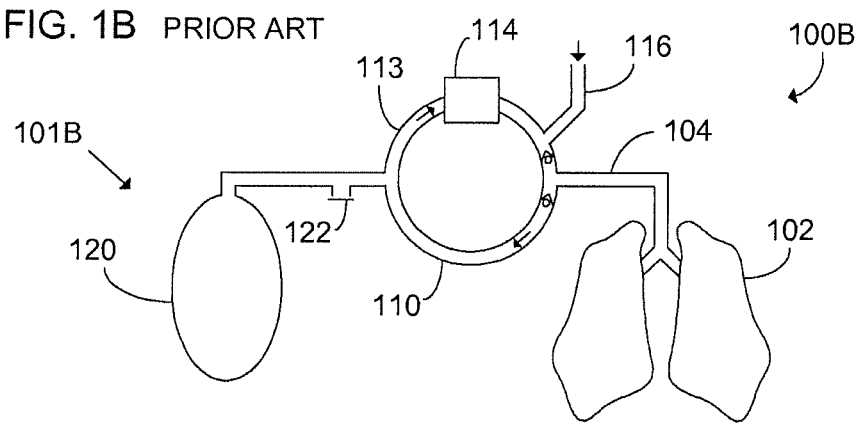
Figure 1C:
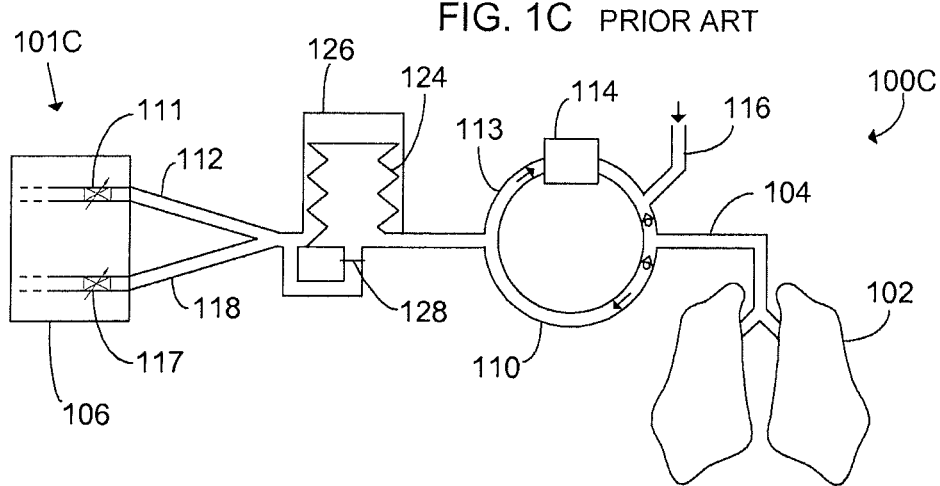

Now, the function of the patient cassette 306 will be described when used in a circle system driven by a manually operated breathing bag or a ventilator operated bag-in-bottle arrangement, i.e. a circle system similar to the circle systems 100B and 100C described in the background portion with reference made to FIGS. 1B and 1C. That is, the inlet 308 should now be regarded as connected to a breathing bag or a bag-in-bottle while the outlets 314a and 314b still should be regarded as connected to an inhalation branch and an exhalation branch, respectively, of a Y-shaped patient connector which at the other end is connected to a patient.

When the patient exhales, exhalation gases will enter the patient cassette 306 via the inlet 314b to which they are conveyed via the exhalation branch of the patient connector. The exhalation gases are then conveyed through the expiratory leg 340 and into the first common-line portion 326 into which they are directed by the two-way valve 336. The exhalation gases then pass through the inlet 308 and into the breathing bag or bag-in-bottle. When inhalation is initiated by compression of the breathing bag or the bag-in-bottle, the exhalation gases are reflected and conveyed back into the patient cassette 306 via the inlet 308. The two-way valve 335 directs the reflected exhalation gases into the first common line portion 326 through which they are conveyed into the inspiratory leg 338. The gases then flows out through the inlet 314a and are re-supplied to the patient via the inhalation branch of the patient connector. Before the exhalation gases leaves the patient cassette 306 through the inlet 314a, CO2 is removed by means of the CO2 absorber 342 and additional fresh gas is added to the gas flow via the fresh gas supply line 348.

When used in a breathing circuit wherein the drive circuit is a breathing bag, the outlet 318 of the patient cassette 306 can be connected to a scavenging system or the like for venting excess gases out of the breathing circuit. In this case, the valve arrangement 350 preferably has an adjustable pressure limiting (APL) valve for setting a highest allowable pressure in the breathing circuit and hence limit the amount of potential pressure build-up that can occur during manual ventilation due to the compression of the breathing bag and the supply of fresh gas. In case the breathing bag or the tubing connecting the breathing tube and the inlet 308 itself comprises an APL valve through which excess gases can be vented out of the breathing circuit, the outlet 318 of the patient cassette 306 is not needed. When used in a breathing circuit wherein the drive circuit is a bag-in-bottle arrangement, the outlet 318 of the patient cassette 306 can be connected to the expiratory portion of the ventilator operating the bag-in-bottle. Then the valve arrangement 350 preferably has a pop-off valve which opens when the bag, i.e. the resilient bellows, in the bag-in-bottle arrangement hits the roof of the container in which it is enclosed. The occurrence of the bag hitting the roof of the container may be sensed by a sensor in the bag-in-bottle arrangement and communicated to the pop-off valve in the valve arrangement 350, or it may be sensed by a pressure sensor in the patient cassette 306 since the pressure in the circle system rises when the bag-in-bottle cannot expand any further. Such a pop-off valve may also be arranged along the gas line connecting the outlet 318 with the expiratory portion of the ventilator. In case the bag-in-bottle arrangement or the tubing connecting the bag-in-bottle arrangement and the inlet 308 itself comprises a pop-off valve through which excess gases can be vented out of the breathing circuit, the outlet 318 of the patient cassette 306 is redundant and may, if still included in the patient cassette 306, be held closed. It should be appreciated that pressure regulating valves, such as PEEP valves, APL valves and pop-off valves are well-known in the art and those skilled in the art know how to arrange a valve arrangement 350 embodying all such valves needed to optimize the functionality of the patient cassette 306 when used with different drive circuits and in different types of breathing circuits. The patient cassette 306 may have one or several user input devices allowing a system operator to choose which valve or combination of valves in the valve arrangement 350 that should be operative in dependence of the particular drive circuit and breathing circuit type used.

The two-way valves 335, 336 and the first common line portion 326 allows the flow of exhalation gases to bypass the volume reflector 328, 330, 332. Thereby, the patient circuit volume and hence the compressible volume in the patient circuit is minimized. These means for varying the patient circuit volume of the patient cassette 306 thus serve to optimize the patient cassette for use in circle systems driven by manual bags or bag-in-bottle arrangements.

Above, it has been described how the patient cassette 306 according to the invention can be optimized for use in circle systems driven by different types of drive circuits and for different patients having different tidal volumes. By minimizing the patient circuit volume, the patient cassette 306 can be advantageously used in circle systems wherein a manual bag or a bag-in-bottle arrangement is used as drive circuit. By increasing the volume of the common line in the patient circuit, a volume reflector formed by the common-line portion 328, 330, 332 is introduced, allowing the patient cassette 306 to also be advantageously used in a circle system of volume reflector type. By allowing the volume of the introduced volume reflector to be varied, said volume reflector can be optimized to different patients having different tidal volumes.

Furthermore, the patient cassette 306 according to the invention can be optimized for use in breathing circuits of anesthetic reflector type, such as the one described in the background portion with reference made to U.S. Pat. No. 5,471,979. This is achieved by minimizing the volume of the patient circuit as described above, arranging an anesthetic reflector, such as an anesthetic adsorption filter 352, in the first common-line portion 326 of the patient circuit, and connecting the outlet 318 to an expiratory portion of a ventilator, or to a scavenging or recovery system. Breathing gas may then be supplied to the by a direct-acting ventilator, through inlet 308, and conveyed to the patient via the first common-line portion 326. During exhalation, the exhalation gases are conveyed via the first common-line portion 326 to the outlet 318 through witch they are vented out of the breathing circuit. Before leaving the breathing circuit, anesthetic gases in the exhalation gases are adsorbed by the adsorption filter and, when fresh breathing gas passes the anesthetic reflector 352 during the following inhalation phase, the anesthetic gases are desorbed and re-supplied to the patient. A PEEP valve arranged either in the expiratory portion of the ventilator or in the valve arrangement 350 can be used to apply a PEEP to the patient during the exhalation phase. This breathing circuit type can also be used during manual ventilation by means of a manual breathing bag. When a breathing bag is used as drive circuit instead of a ventilator, the valve arrangement 350 can comprise an APL valve, or, the PEEP valve in the ventilator may be re-configured to serve as an APL valve. As previously mentioned when the patient cassette 306 has been described during use in other types of breathing circuits, the outlet for exhalation gases could as well be comprised in the drive circuit. In such a case, the outlet 318 is redundant and can, if still included in the patient cassette 306, be held closed.

That is, when the patient cassette 306 is connected to a direct-acting ventilator, a volume reflector system capable of re-supplying the majority portion of all gases exhaled by the patient can be provided by directing the exhalation gases into the volume reflector 328, 330, 332 from which they are pushed back to the patient by a drive gas flow supplied by said ventilator. On the other hand, by directing the exhalation gases through the first common-line portion 326 in which an anesthetic reflector 352 is arranged, and hence bypass the volume reflector formed by the common-line portion 328, 330, 332, an anesthetic reflector system can be provided. In this case, the drive gas provided by the ventilator becomes breathing gas and the fresh gas flow supplied through the fresh gas supply line can be adjusted to only supply anesthetic or other additive gases. Thereby, the compressible volume in the breathing circuit is greatly reduced while the loss of anesthetic gases one would like to re-supply to the patient only is marginally increased. This possibility of changing from a volume reflector system to an anesthetic reflector system in a simple and quick manner is particularly important when it comes to ventilate patients with small tidal volumes and when the ventilation parameters are critical, in which case the importance of a small compressible volume in the breathing circuit is significant.

Additionally, an anesthetic reflector (not shown) is also arranged in the second common-line portion 328, 330, 332 which, when the patient cassette 306 is used in a volume reflector system, constitutes the volume reflector. According to a preferred embodiment, the volume-variable portion 330 of the volume reflector is a conventional breathing tube which is wholly or partially stuffed with a material that adsorbs anesthetic gases. The anesthetic adsorbing material could, for example, be active carbon fabric or granulate. When the exhalation gases passes through the volume-variable portion of the volume reflector 328, 330, 332, the anesthetic gases is adsorbed by the adsorption material, and when the exhalation gases are re-supplied to the patient during the following inhalation, the anesthetic gases are desorbed and re-supplied to the patient. Thus, such a combined volume reflector and anesthetic reflector serves to prevent anesthetic in the exhalation gases from being evacuated from the circle system even if the volume reflector happens to be a little bit too small in relation to the tidal volume of the ventilated patient. If so, the degree of anesthetic reflection and the flow resistance within said breathing tube is dependent on the degree of compaction of the anesthetic adsorbing material.

Figure 4:
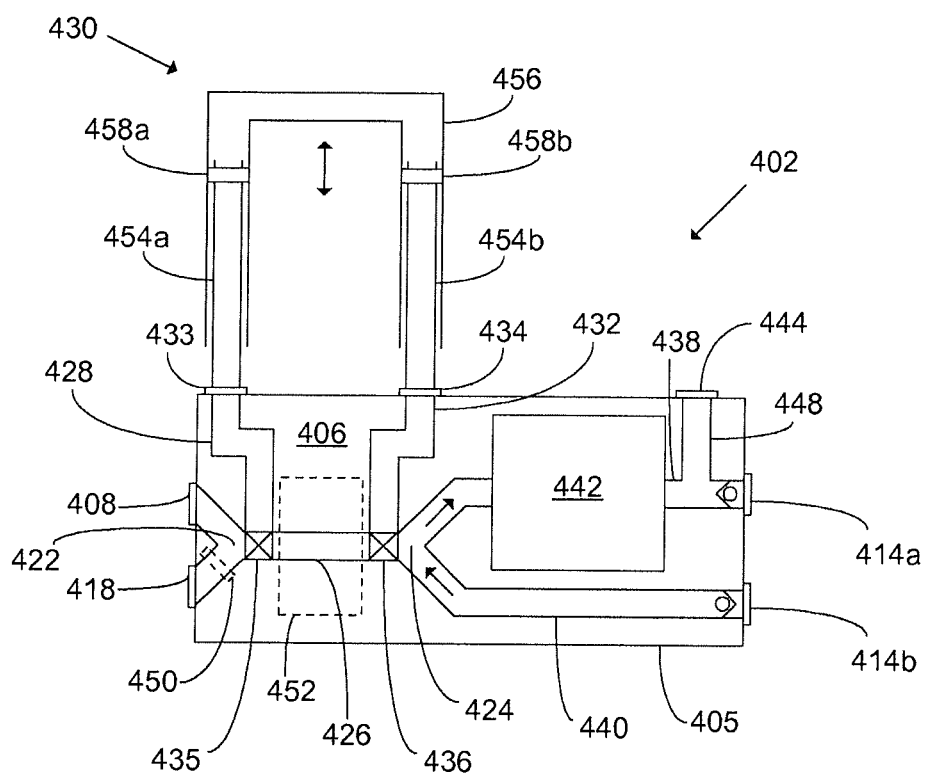

With reference now made to FIG. 4, a patient circuit module 402 is illustrated. In FIG. 4, reference numerals 402, 405, 408, 414*a*, 414*b*, 422, 424, 426, 435, 436, 438, 440, 442, 444, 450 and 452 are used to represent components that are identical to the corresponding reference numerals in FIG. 3 ending in the same last two digits and beginning with "3". The design and the function of the patient circuit module 402 corresponds in all essentials to the patient circuit module 302 described above with reference made to FIG. 3 and differs only in the design of a volume-variable portion 430 of the volume reflector formed by 428 and 432 together with the volume-variable portion 430. In this embodiment, the volume-variable portion 430 includes gas conduits 454*a*-*b*, 456 that overlap each other to form a telescopic slide so as to allow the volume of the portion 430 to be varied by altering the degree of overlapping. The arrangement can be compared with a trombone in which a similar telescopic slide is used to create different tones. The volume-variable portion 430 of the volume reflector formed by 428, 430, 432 comprises two vertical gas conduits 454*a* and 454*b* which are connected to the third 433 and the fourth 434 inlet of the patient cassette 406. The two "legs" of a gas conduit 456, shaped as a 'U' turned upside-down, is arranged to externally overlap the gas conduits 454*a*-*b* at least partially. Preferably, hermetically sealing membranes 458*a*-*b* are arranged close to the ends of the conduits 454*a* and 454*b* to stop potential gas leakage between them and the legs of the U-shaped conduit 456. By moving the gas conduits 458*a* and 458*b* up and down, as illustrated by a double arrow in the drawing, the degree of overlapping between the gas conduits 454*a* and 454*b* and the gas conduit 456, and hence the volume of the volume reflector can be continuously varied. Thereby, the volume of the volume reflected formed by 428, 430, 432 can be adjusted to suit the currently ventilated patient.

Figure 5:
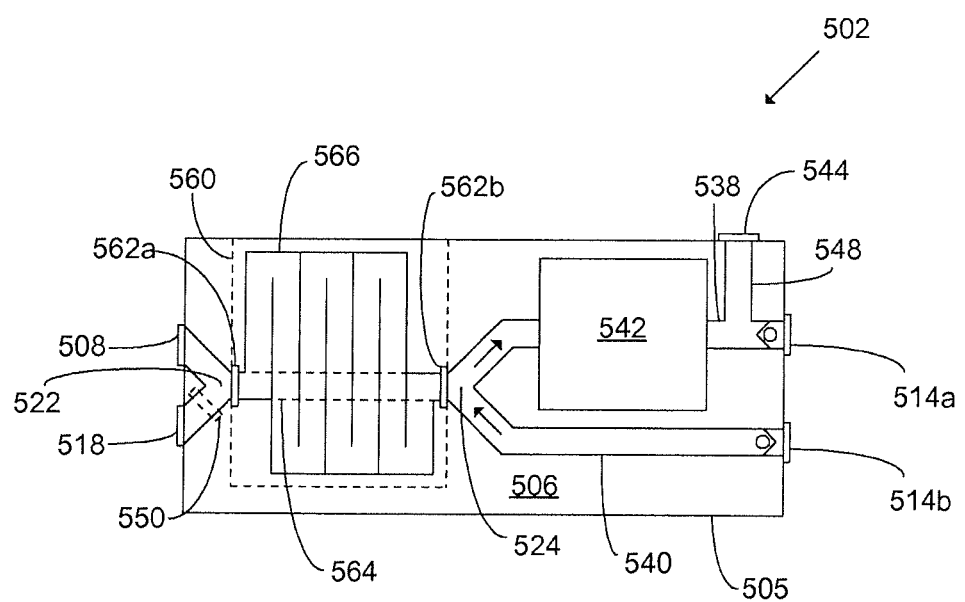

In FIG. 5, another embodiment of a patient cassette 506 according to the invention is shown. In FIG. 5, reference numerals 502, 508, 514a, 514b, 538, 540, 542, 544 and 550 are used to indicate components identical to the corresponding components shown in FIG. 3 ending in the same last two digits, and beginning with "3". In this embodiment, the patient cassette housing 505 comprises a lid 560 which is openable to expose two connection arrangements 562a-b in the interior of the patient cassette 506. The first 562a and second 562b connection arrangements are arranged in the common line of the patient circuit and is hence pneumatically connected to the first branch point 522 and the second branch point 524, respectively. The connection arrangements 562a-b allows different gas conduits 564, 566 with different volumes to be detachably connected there between to form a volume-variable portion of the common line of the patient circuit. By inter-connecting a gas conduit 564 with a small volume between the connection arrangement 562a-b, the patient circuit volume is minimized to optimize the patient cassette 506 for use in a circle system driven by a manual bag or a bag-in-bottle arrangement, or for use in an anesthetic reflector system. By inter-connecting a gas conduit 566 with a larger volume between the connection arrangement 562a-b, which volume is based on the tidal volume of the ventilated patient, a perfectly sized volume reflector is introduced, optimizing the patient cassette 506 for use in a volume reflector system.

By "hiding" the volume-variable portion of the patient circuit internal to the housing 505 of the patient cassette 506, the patient cassette can be made compact and easily movable. By providing the patient cassette with a lid 560 or by other means make sure that the connection arrangement 562a-b is easily accessible, the volume of the patient circuit can be manually varied in a simple way.

Figure 6:
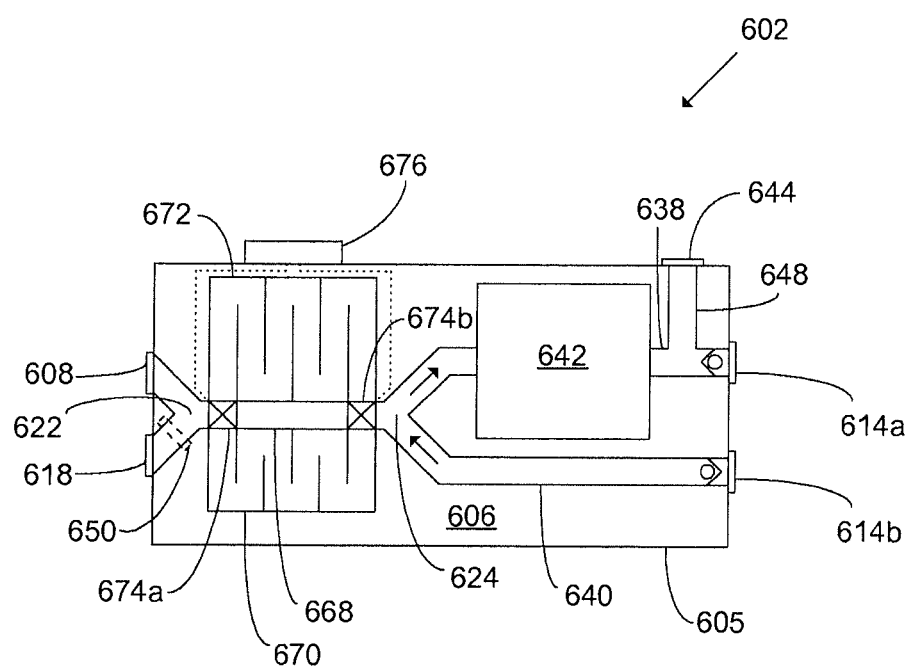

FIG. 6 shows yet another embodiment of a patient cassette 606 according to the invention. In FIG. 6, reference numerals 602, 605, 608, 614a, 614b, 622, 624, 638, 640, 642, 644 and 650 are used to indicate components that are identical to the components shown in FIG. 3, ending in the same last two digits and beginning with "3". In this embodiment, the patient cassette 606 has an arrangement formed by flow paths 668, 670, 672, and valves 674a-b, for varying the volume of the patient circuit automatically. At least a part of the common line of the patient circuit has multiple parallel gas flow paths 668, 670, 672. Two three-way valves, or volume-selector valves 674a-b are arranged to direct the gas flow within the patient circuit through one of said gas flow paths 668, 670, 672. By directing the gas flow through a gas flow path 668 having a very small volume, the volume of the patient circuit can be minimized. By directing the gas flow through a gas flow path 672 having a larger volume, a volume reflector is introduced thus allowing the patient cassette 606 to be used in a volume reflector system. By connecting a plurality of parallel gas flow paths 668, 670, 672 with different volumes in series with the common line of the patient circuit, the gas flow can hence be directed into a gas flow path making the total volume of the volume reflector well-suited for the currently ventilated patient. For example, gas flow path 672 can be chosen for an adult patient and gas flow path 670 can be chosen for a pediatric patient. Although only three different gas flow paths are shown in FIG. 6, it should be appreciated that more parallel gas flow paths having different volumes may be used so as to more exactly adapt the volume of the volume reflector to the currently ventilated patient. Another way to allow the volume of the volume reflector to be more exactly adapted to the tidal volume of the patient is to connect a plurality of parallel gas flow sections, such as the section constituted by the gas conduits forming flow paths 668, 670 and 672, in series inline with the common line of the patient circuit. By having each such section comprise gas conduits with different volumes, various volume combinations can be achieved by directing the gas flow through different gas conduits in the different sections connected in series.

In this embodiment, the patient cassette 606 further comprises a control device 676 for controlling the volume-selector valves 674a-b and thus the volume of the patient circuit. The control device comprises a user input device, such as a rotary control knob, or a graphical user interface, such as a touch screen, to allow a system operator to control the volume selector valves 674a-b and thereby adjust the patient circuit system volume based on the tidal volume of the currently ventilated patient.

Figure 7:
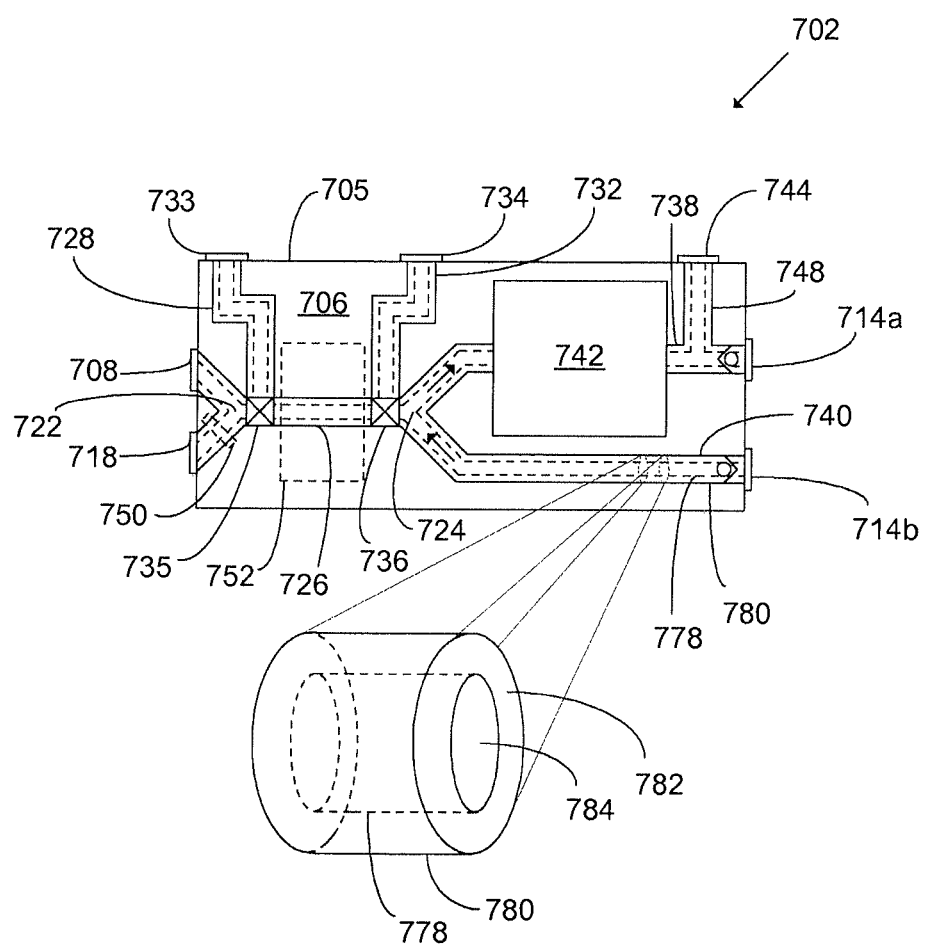

With reference now made to FIG. 7, another embodiment of a patient cassette 706 according to the invention is shown. In FIG. 7, reference numerals 702, 705, 714a, 714b, 722, 724, 728, 732, 736, 742, 744, 750 and 752 are used to indicate components identical to the components in FIG. 3 ending in the same last two digits, and beginning with "3". The patient cassette 706 is identical to the patient cassettes 306, 406 shown in FIGS. 3 and 4 besides that the patient circuit is made of "coaxial" gas tubes (and besides that there is no gas container connected between the third 733 and the fourth 734 outlets of the patient cassette). The gas line forming the patient circuit comprises a thin, inner gas conduit 778 which is surrounded by a thicker, outer gas conduit 780 so that a gas flow path 782 is formed between the two gas conduits 778, 780. Typically, the gas conduits 778 and 780 are two circular tubes that are coaxially aligned. The inlets of the patient cassette 706 comprise means (not shown) for directing the gas flow received via the inlets into either the gas flow path 784 inside the inner gas conduit 778, the gas flow path 782 formed between the inner 778 and the outer 780 gas conduit, or into both of said gas flow paths 782, 784. Thereby, the patient circuit volume can be varied in three different ways. Typically, it is desirable to have a small patient circuit volume so as to minimize the compressible volume in the breathing circuit. However, it is also desirable to use thick gas conduits in order to minimize the flow resistance within the breathing circuit. When ventilating really small patients, increased flow resistance in the breathing circuit is not as crucial to the system performance as when ventilating big patients with large tidal volumes. Therefore, it may be desirable to use both gas flow paths 782, 784 when ventilating adult patients while using only one of them when ventilating infant patients. Of course, only parts of the patient circuit could be composed by coaxial tubes 778, 780. For example, coaxial tubes may be used only between the inlet 708 and the first two-way valve 735, in the first common-line portion 726, and in the inspiratory 738 and expiratory 740 legs since this is the gas flow path typically used when ventilating patients with really small tidal volumes.

The patient cassette 306, 406, 506, 606, 706 according to the invention can also be optimized for being used in an open, non-rebreathing circuit. This is preferably achieved by delivering the breathing gas through the gas supply line 348, 448, 548, 648, 748 which otherwise is used for delivering a fresh gas flow, and venting the exhalation gases out of the breathing circuit via the outlet 318, 418, 518, 618, 718. Thereby, a breathing circuit with a minimum of compressible volume is provided. This type of breathing circuit may be used when ventilating infant patients being so small that the amount of anesthetic in the exhalation gases is negligible and the demand for a small compressible volume in the breathing circuit is crucial.

According to the invention, a patient cassette for use in a modular breathing circuit comprises means for varying the volume of the patient circuit. As described above, this volume may be manually set by a medical professional or automatically set by control means in the patient cassette. In both cases, the volume may be set based on measurement values measured by various sensors, such as pressure and flow sensors, disposed in the patient cassette or elsewhere in the breathing circuit to which the patient cassette is connected. For example, a flow sensor can be used to measure the tidal volume of the patient connected to the system. If the measured tidal volume is small, the patient circuit volume can be minimized. If the patient cassette is to be used in a volume reflector system, the volume of the volume-variable volume reflector can be set to a volume equal to or slightly bigger than the established tidal volume of the patient. Another way to make sure that the volume of the volume reflector has been chosen correctly is to measure the gas flow (and thereby the gas volume) that is pushed out of the volume reflector during exhalation. This volume should be as close as possible to the delivered drive gas volume (typically, it is slightly bigger than the delivered drive gas volume due to the added fresh gas). When setting the volume of the volume reflector based on measured tidal volume of the patient, the latter method can still be employed as a precautionary measure.

The above described methods for optimizing the patient circuit volume in relation to the tidal volume of the patient are preferably continuously or at least repetitively performed during ongoing anesthesia treatment. When patients suffering from certain lung diseases are subject to artificial ventilation, the tidal volume may change rapidly due to physical changes in the pulmonary system of the patient. Therefore, there may be a need to vary the volume of the patient circuit also during ongoing anesthesia treatment.

The patient cassette 206, 306, 406, 506, 606, 706 has herein been described as comprising a fresh gas inlet and a fresh gas supply line, a CO2 absorber, and additionally an outlet for excess exhalation gases, typically comprising one or several pressure regulating valves, such as an APL, pop-off, or PEEP valve. It should however be appreciated that although these components typically are included in a regular patient cassette, they do not have to form a part of the patient cassette according to the invention. For example, the fresh gas can be supplied directly to the inhalation branch of the patient connector, and the outlet and valves for excess exhalation gases can be disposed in the drive circuit to which the patient cassette is connected, as previously described. Likewise, the patient cassette can include various components and parts of the breathing system which has not been described herein. For example, the patient cassette according to the invention may comprise additional gas flow paths and additional valves for regulating the flow and the pressure within the breathing circuit. It may also comprise additional sensors and safety devices not mentioned herein.

Although the invention has herein been described with reference to specific embodiments, these descriptions are hence not meant to be construed in a limiting sense. Various modifications of the disclosed embodiments, as well as alternative embodiments of the invention will become apparent to persons skilled in the art upon reference to the description of the invention. It is therefore contemplated that such modifications do not depart from the scope of the invention as set forth in the appended claims.

We claim as our invention:

1. A patient cassette for use in a modular rebreathing circuit that provides breathing assistance to a patient, said modular rebreathing circuit being of a breathing circuit type, from among a plurality of different breathing circuit types, said patient cassette comprising:

a cassette housing having a first inlet configured for connection to a drive circuit that forces gas through said first inlet, said drive circuit being of a drive circuit type, from among a plurality of different drive circuit types;

a patient circuit in said cassette housing pneumatically connected to said first inlet, said patient circuit comprising a Y-branch having an expiratory line connected to a second inlet of said cassette housing configured to receive expiratory gas from the patient, and an inspiratory line connected to an outlet of said cassette housing configured to provide gas from said drive circuit to the patient, and a volume-varying arrangement connected between said first inlet and said Y-branch to form a part of said patient circuit in said cassette housing between said first inlet and said Y-branch, said volume-varying arrangement having a selectable volume that, when set, also sets a volume of said patient circuit to a set volume dependent on at least one of: the drive circuit type of the drive circuit currently connected to said first inlet, the breathing circuit type of the modular rebreathing circuit comprising said drive circuit currently connected to said first inlet, and a predetermined tidal volume of the patient currently connected to said outlet.

2. A patient cassette as claimed in claim 1 wherein said volume-varying arrangement comprises a connector configured to allow detachable connection of different gas containers to said patient circuit, said different gas containers having respectively different volumes.

3. A patient cassette as claimed in claim 2 wherein said connector of said volume-varying arrangement is configured to connect said different gas containers externally of said patient cassette.

4. A patient cassette as claimed in claim 1 comprising a third inlet pneumatically connected to said first inlet and a fourth inlet pneumatically connected to said second inlet, said third inlet and said fourth inlet being configured for connection to gas containers having respectively different volumes, and forming said volume-varying arrangement.

5. A patient cassette as claimed in claim 1 wherein said patient circuit comprises a common line which is configured to convey gas both to and from the patient connected to the patient connector that is currently connected to said second inlet, said common line having a common line volume, and said volume-varying arrangement being configured to vary said common line volume in order to set said set volume.

6. A patient cassette as claimed in claim 5 wherein said common line comprises a first common line portion and a second common line portion, and wherein said patient cassette comprises a plurality of valves operable to direct a gas flow through said common line through either of said first common line portion or said second common line portion, said first common line portion having a small volume that minimizes said volume of said patient circuit and said second common line portion having a volume such that said common line volume is equal to at least an average tidal volume.

7. A patient cassette as claimed in claim 6 wherein said volume of said second common line portion is variable.

8. A patient cassette as claimed in claim 1 comprising a $CO_2$ absorber in said cassette housing, connected in said expiratory line of said Y-branch.

9. A patient cassette as claimed in claim 8 wherein said cassette housing comprises a fresh air inlet pneumatically connected to said expiratory line, between said $CO_2$ absorber and said outlet.

10. A modular rebreathing circuit comprising:

a modular rebreathing circuit configuration, said configuration giving said modular rebreathing circuit a breathing circuit type, from among a plurality of different breathing circuit types;

a drive circuit module of a drive circuit module type from among a plurality of different drive circuit types;

a patient connector; and a patient cassette, said patient cassette comprising a cassette housing having:

- a first inlet configured for connection to a drive circuit that forces gas through said first inlet, said drive circuit being of a drive circuit type, from among a plurality of different drive circuit types,
- a patient circuit in said cassette housing pneumatically connected to said first inlet, said patient circuit comprising a Y-branch having an expiratory line connected to a second inlet of said cassette housing configured to receive expiratory gas from the patient, and an inspiratory line connected to an outlet of said cassette housing configured to provide gas from said drive circuit to the patient, and
- a volume-varying arrangement also connected between said first inlet and said Y-branch to form a part of said patient circuit between said first inlet and said Y-branch, said volume-varying arrangement having a selectable volume that, when set, also sets a volume of said patient circuit volume, said volume-varying arrangement being configured to vary said patient circuit volume dependent on at least one of: the drive circuit type of the drive circuit currently connected to said first inlet, the breathing circuit type of the modular rebreathing circuit comprising said drive circuit currently connected to said first inlet, and a predetermined tidal volume of the patient currently connected to said patient connector via said outlet and said second inlet.

11. A modular rebreathing circuit as claimed in claim 10 comprising:

a $CO_2$ absorber in said cassette housing connected in said expiratory line of said Y-branch.

12. A modular rebreathing circuit as claimed in claim 11 wherein said cassette housing comprises a fresh air inlet pneumatically connected to said expiratory line, between said $CO_2$ absorber and said outlet.

* * * * *